(12) United States Patent
Bryan

(10) Patent No.: US 6,749,635 B1
(45) Date of Patent: Jun. 15, 2004

(54) PEANUT SPECTACLE MULTI DISCOID THORACO-LUMBAR DISC PROSTHESIS

(75) Inventor: Vincent Bryan, Mercer Island, WA (US)

(73) Assignee: SDGI Holdings, Inc., Wilmington, DE (US)

( * ) Notice: Subject to any disclaimer, the term of this patent is extended or adjusted under 35 U.S.C. 154(b) by 0 days.

(21) Appl. No.: 09/786,073

(22) PCT Filed: Sep. 3, 1999

(86) PCT No.: PCT/US99/20457

§ 371 (c)(1),
(2), (4) Date: Jun. 19, 2001

(87) PCT Pub. No.: WO00/13619

PCT Pub. Date: Mar. 16, 2000

Related U.S. Application Data

(60) Provisional application No. 60/099,277, filed on Sep. 4, 1998.

(51) Int. Cl.⁷ .................................................. A61F 2/44
(52) U.S. Cl. .................................................. 623/17.16
(58) Field of Search ........................ 623/17.11, 17.15, 623/14.12, 17.12, 17.16; 606/61

(56) References Cited

U.S. PATENT DOCUMENTS

| | | |
|---|---|---|
| 2,677,369 A | 5/1954 | Knowles |
| 4,599,086 A | 7/1986 | Doty |
| 4,645,507 A | 2/1987 | Engelbrecht et al. |
| 4,714,469 A | 12/1987 | Kenna |
| 4,757,983 A | 7/1988 | Ray et al. |
| 4,759,766 A | 7/1988 | Buettner-Janz et al. |
| 4,759,769 A | 7/1988 | Hedman et al. |
| 4,766,328 A | 8/1988 | Yang |
| 4,777,942 A | 10/1988 | Frey et al. |
| 4,800,639 A | 1/1989 | Frey et al. |
| 4,834,757 A | 5/1989 | Brantigan |
| 4,878,915 A | 11/1989 | Brantigan |
| 4,887,595 A | 12/1989 | Heinig et al. |
| 4,908,032 A | 3/1990 | Keller |
| 4,908,036 A | 3/1990 | Link et al. |

(List continued on next page.)

FOREIGN PATENT DOCUMENTS

| | | |
|---|---|---|
| DE | 2263842 | 7/1974 |
| DE | 2804936 | 8/1979 |
| DE | 90 00 094.3 | 4/1990 |
| EP | 0176728 | 4/1986 |
| EP | 00560140 A1 | 9/1993 |
| SU | 895433 | 1/1982 |
| SU | 1560184 | 4/1990 |

OTHER PUBLICATIONS

International Search Report for International Application No. PCT/US 01/24791.

Brain et al.; "The Neurological Manifestations of Cervical Spondylosis;" Brain: A Journal of Neurology, vol. 75; Macmillan & Co.; 1952; pp. 187–225.

(List continued on next page.)

*Primary Examiner*—Brian E. Pellegrino
(74) *Attorney, Agent, or Firm*—Haynes & Boone, LLP

(57) ABSTRACT

A small profile, peanut spectacle-shaped prosthetic disc device is provided. The device housing is comprised of two longitudinally split hollow halves, between which are contained multiple discoid shaped resilient bodies which may be of a polymeric type, or they may contain hydrogel. These bodies may lie in concave surfaces located on the interior of each side of the split cylindrical housing. The housing halves, even under maximum physiological loads, do not contact one another directly. The shell shape permits relatively easy introduction of the implant into inter-vertebral spaces in the thoracic or lumbar region of the human spine.

3 Claims, 2 Drawing Sheets

U.S. PATENT DOCUMENTS

| | | | |
|---|---|---|---|
| 4,911,718 A | | 3/1990 | Lee et al. |
| 4,917,704 A | * | 4/1990 | Frey et al. ............... 623/17.16 |
| 4,932,969 A | | 6/1990 | Frey et al. |
| 4,978,355 A | | 12/1990 | Frey et al. |
| 5,059,193 A | | 10/1991 | Kuslich |
| 5,084,048 A | | 1/1992 | Jacob et al. |
| 5,122,130 A | | 6/1992 | Keller |
| 5,171,281 A | | 12/1992 | Parsons et al. |
| 5,176,708 A | | 1/1993 | Frey et al. |
| 5,192,326 A | | 3/1993 | Bao et al. |
| 5,192,327 A | | 3/1993 | Brantigan |
| 5,234,431 A | | 8/1993 | Keller |
| 5,246,458 A | | 9/1993 | Graham |
| 5,261,911 A | | 11/1993 | Carl |
| 5,261,913 A | | 11/1993 | Marnay |
| 5,306,308 A | | 4/1994 | Gross et al. |
| 5,314,477 A | | 5/1994 | Marnay |
| 5,344,459 A | * | 9/1994 | Swartz ..................... 623/14.12 |
| 5,370,697 A | | 12/1994 | Baumigartner |
| 5,383,933 A | | 1/1995 | Keller |
| 5,403,314 A | | 4/1995 | Currier |
| 5,425,772 A | | 6/1995 | Brantigan |
| 5,425,773 A | | 6/1995 | Boyd et al. |
| 5,443,514 A | | 8/1995 | Steffee |
| 5,456,719 A | | 10/1995 | Keller |
| 5,458,638 A | | 10/1995 | Kuslich et al. |
| 5,489,308 A | | 2/1996 | Kuslich et al. |
| 5,496,318 A | | 3/1996 | Howland et al. |
| 5,527,315 A | | 6/1996 | Jeanson et al. |
| 5,534,029 A | | 7/1996 | Shima |
| 5,534,030 A | | 7/1996 | Navarro et al. |
| 5,545,229 A | | 8/1996 | Parsons et al. |
| 5,549,679 A | | 8/1996 | Kuslich |
| 5,556,431 A | | 9/1996 | Buttner-Janz |
| 5,562,738 A | | 10/1996 | Boyd et al. |
| 5,571,189 A | | 11/1996 | Kuslich |
| 5,609,636 A | | 3/1997 | Kohrs et al. |
| 5,649,926 A | | 7/1997 | Howland |
| 5,658,285 A | | 8/1997 | Marnay et al. |
| 5,662,158 A | * | 9/1997 | Caldarise .................... 164/456 |
| 5,674,294 A | * | 10/1997 | Bainville et al. ........ 623/17.16 |
| 5,674,296 A | * | 10/1997 | Bryan et al. ................... 606/61 |
| 5,676,701 A | | 10/1997 | Yuan et al. |
| 5,713,899 A | | 2/1998 | Marnay et al. |
| 5,716,415 A | | 2/1998 | Steffee |
| 5,723,013 A | | 3/1998 | Jeanson et al. |
| 5,782,832 A | * | 7/1998 | Larsen et al. ............... 606/612 |
| 5,888,197 A | | 3/1999 | Mulac et al. |
| 5,897,087 A | | 4/1999 | Farley |
| 5,902,233 A | | 5/1999 | Farley et al. |
| 5,928,284 A | * | 7/1999 | Mehdizadeh ............. 623/17.13 |
| 5,984,865 A | | 11/1999 | Farley et al. |
| 6,017,008 A | | 1/2000 | Farley |
| 6,033,363 A | | 3/2000 | Farley et al. |
| 6,179,874 B1 | | 1/2001 | Cauthen |

OTHER PUBLICATIONS

Buttner–Janz et al.; "Biomechanics of the SB Charite Lumbar Intervertebral Disc Endoprosthesis;" International Orthopedics; vol. 13; 1989; pp. 173–176.

Edeland; "Some Additional Suggestions for an Intervertebral Disc Prosthesis;" Dept. of Occupational Health; Vdvo PV AB; S–40508; Goteborg; Sweden; 1985 Butterworth & Co. Publishers Ltd.

Enker et al.; "Artificial Disc Replacement;" Spine; vol. 18; No. 8; 1993; pp. 1061–1070.

Hawkins et al.; "Shear Stability of an Elastomeric Disk Spacer Within an Intervertebral Joint: A Parametric Strudy;" Journal of Biomechanical Engineering Technical Briefs; vol. 114; Aug. 1992; pp. 414–415.

Hedman et al.; "Design of an Intervertebral Disc Prosthesis;" Spine; vol. 17; No. 6; 1991; pp. S256–S260.

Hellier et al.; "Wear Studies for Development of an Intervertebral Disc Prosthesis;" Spine; vol. 17; No. 6 Supplement; 1992; pp. S86–S96.

Hodd; "Far Lateral Lumbar Disc Herniations;" Neurosurgery Clinics of North America; vol. 4, No. 1; Jan. 1993; pp. 117–124.

Langrana et al.; "Finite–Element Modeling of the Synthetic Intevertebral Disc;" Spine; vol. 16; No. 6: 1991; pp. S245–S252.

Lee et al.; "Development of a Prosthetic Intervertebral Disc;" Spine; vol. 16; No. 6; 1991; pp. S253–S255.

Lee et al.; "Natural History & Prognosis of Cervical Spondylosis;" British Medical Journal; Dec. 28, 1963; British Medical Association, London, England; Copyright 1963; pp. 1607–1610.

Long; "Failed Back Surgery Syndrome;" Neurosurgery Clinics of North America; vol. 2, No. 4; Oct. 1991; pp. 899–919.

Ray; "The Artifical Disc—Introduction, History and Socioeconomics;" Clinical Efficacy and Outcome in the Diagnosis and Treatment of Low Back Pain; Raven Press, Ltd., NY; 1992; pp. 205–280.

Robinson et al.; The Results of Anterior Interbody Fusion of the Cervical Spine, The Journal of Bone & Joint Surgery; vol. 44–A, No. 8, Dec. 1962; pp. 1569–1587.

Simeone and Rothman; "Cervical Disc Disease;" Pennsylvania Hospital & University of Pennsylvania; 1975; pp. 387–433.

Solini et al.; "Metal Cementless Prosthesis for Vetebral Body Replacement of Metastatic Malignant Disease of the Cervical Spine;" Journal of Spinal Disorders; vol. 2; No. 4; 1989; pp. 254–262.

Solini et al.; "Protesi Somatica Cervicale;" Ingegneria Ricostruttiva D'Avanguardia; Howmedica International; Pfizer; Italy.

Taylor, Collier;, "The Occurence of Optic Neuritits in Lesions of the Spinal Cord, Injury, Tumor, Melitis;" Brain: A Journal of Neurology; vol. 24; Macmillian & Co. Ltd., 1901; pp. 532–550.

Tie–sheng et al.; "Lumbar Intervertebral Disc Prosthesis;" Chinese Medical Journal, 104–(5); 1991; pp. 381–386.

* cited by examiner

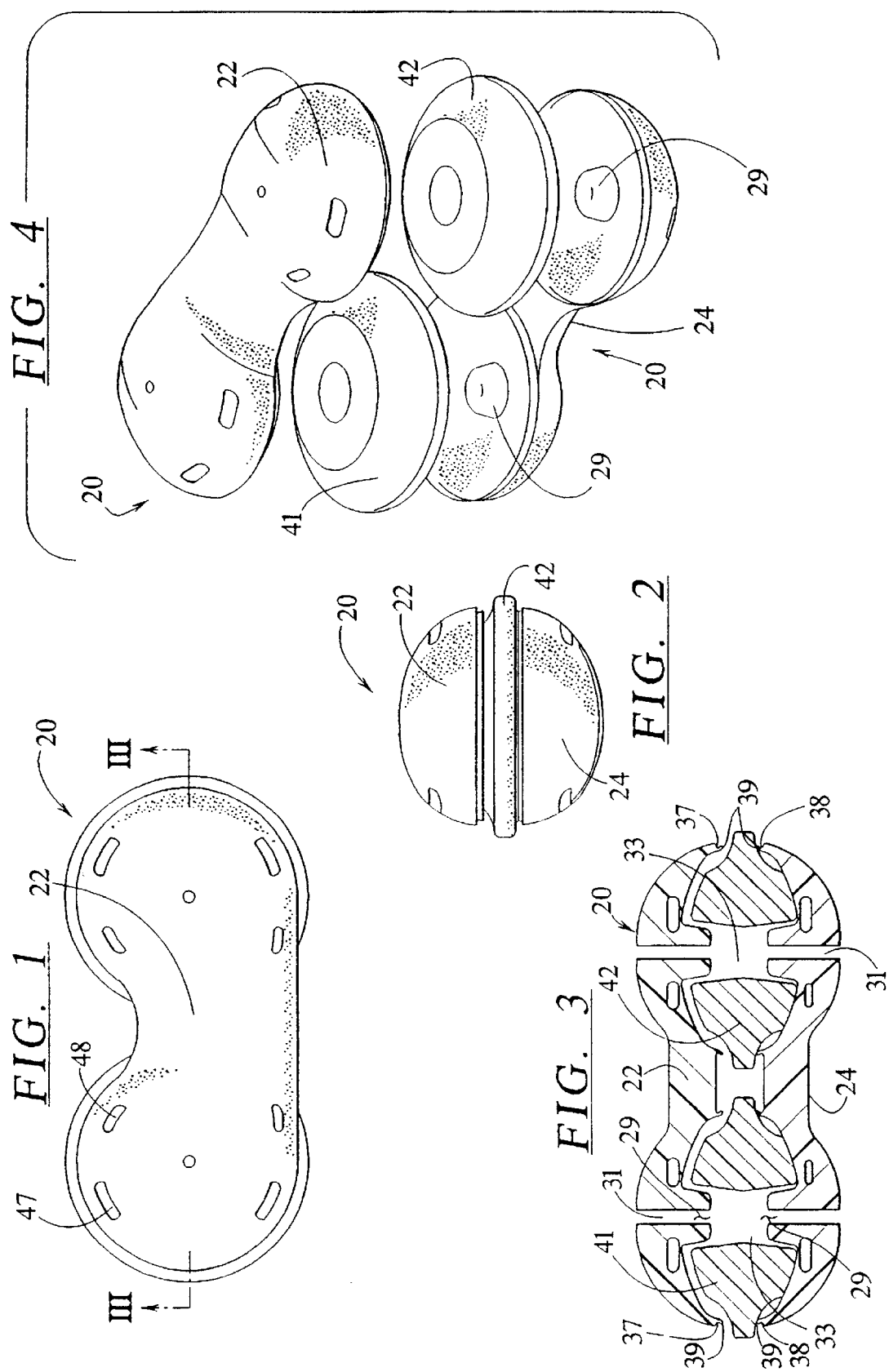

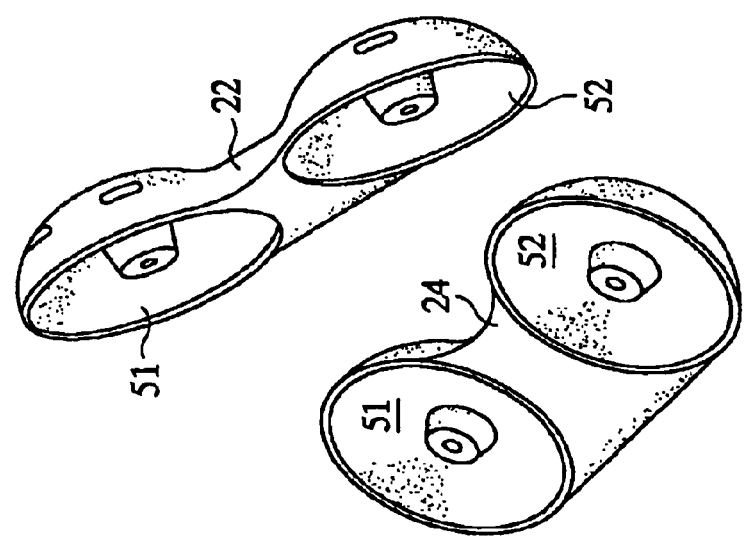
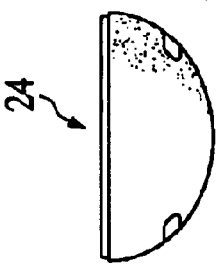
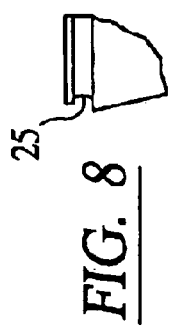
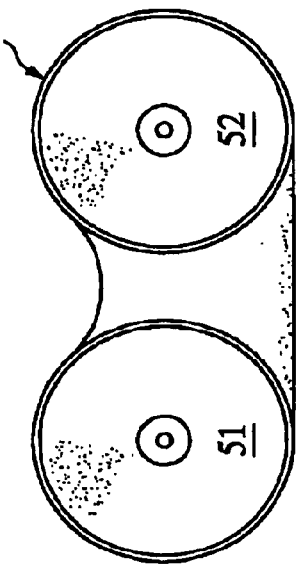
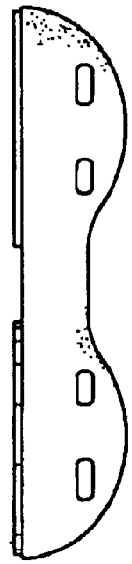

PEANUT SPECTACLE MULTI DISCOID THORACO-LUMBAR DISC PROSTHESIS

This application is a 371 of PCT/US99/20457 Sep. 30, 1999 which claims benefit of U.S. Ser. No. 60/099,277 Sep. 4, 1998.

This invention relates to the design and use of a unique disc prosthesis for the lumbar and thoracic spine. By placing one or more ovoid resilient prosthetic nuclei in series inside a peanut-shaped housing of metal ceramic or polymeric material, which housing is shaped so that it is separated into two sections longitudinally, a thin profile prosthesis can be created which will allow placement of the device through a small opening for implant into the thoracic or lumbar portion of the spine.

U.S. Pat. No. 5,674,296 is incorporated by reference.

BACKGROUND OF THE INVENTION

Degenerative disc disease, including disc herniation, may produce disabling symptoms of local pain, radiculopathy or myelopathy in an otherwise clinically stable spine, and may be unresponsive to non-surgical treatment. Several surgical treatments are available to address the symptoms of degenerative disc disease when non-invasive therapies are not effective. These surgical treatments include decompression, discectomy and fusion. These treatments, and in particular the discectomy and fusion procedures, provide relief of clinical symptoms but they do not restore normal or near normal range of motion or cushioning to the affected functional spinal unit (FSU). This can result in acceleration of the degenerative process in spinal discs adjacent to the original surgical operation site. This degenerative process can, in turn, require additional surgical intervention.

Open surgery and endoscopic techniques are often used to provide access to the targeted intervertebral disc space. Posterior, postero-lateral, and anterior approaches allow placement of instrumentation to facilitate exposure of the degenerated disc and the insertion of bone grafts or fusion cages to accomplish bony fusion.

Because of anatomical structure considerations and instrument size restrictions associated with minimally invasive surgical techniques in the anterior lumbar spine, the insertion of a functional disc prosthesis equal in size to the natural disc creates risks due to mechanical interferences with critical vascular structures.

A functional disc prosthesis which provides for a full range of motion of the FSU and for cushioning between two adjacent vertebrae while maintaining stability, intervertebral body spacing and lordosis, is desirable.

More specifically it is an object of the invention to provide a disc prosthesis having a small or narrow profile. The novel exemplary prosthesis has an exterior shape like that of a peanut shell. This peanut shaped housing is comprised of two longitudinally split halves. Each housing half is separated from the other at all times by disk shaped resilient bodies contained therein, and is strong enough to support the loads to which it shall be subjected during the activities of daily living. The discoid nuclei are of smaller diameter than the natural discs they replace, and are positioned in the shell concave interiors of the peanut shaped housing. The housing is configured to accommodate the restrictions imposed by the limited anatomical space available for the surgical placement of the implant, and is small so as to utilize implantation procedures and instrumentation such as those used in an endoscopic procedure.

It is a further object of the invention to provide geometry to engage concave mating surfaces on the vertebral bodies or bones so as to provide proper stability and proper positioning of the opposing engaged vertebrae or vertebral bodies.

Another object is to obviate the need for a second surgical site for bone graft harvesting as may be required when spinal fusion cages are implanted.

And it is a further object of the invention to provide a sheath so as to completely surrounded and enclose the space occupied by the resilient bodies between the two housing halves, thereby restricting the migration of debris outside the prosthesis, restricting cancellous tissue ingrowth into the device, and providing a sealed space around the prosthetic nucleus in which lubricant may be contained.

Still another object of the invention is to provide a disc prosthesis which will permit motion between the housing halves.

A further object of the intention is to provide a disc prosthesis which will provide for cushioning between the housing halves.

It is a still further object of the invention to provide a disc prosthesis which may be used alone or in parallel array with similar prostheses.

It is yet another object to provide a housing having one or more ports through which a liquid (for example, a saline fluid, hyaluronic acid, or similar lubricating fluid material including for example a hydrogel material) can be introduced into the housing interior space confined within the sheath and partly occupied by the disc for purposes of lubrication, spacing, and/or cushioning. A plug, screw or other can also be provided to seal closed the port following introduction of that material.

Other objects and advantages of the invention will become apparent to those skilled in the art upon reading the following detailed description and upon reference to the drawings. Throughout the drawings, like reference numerals refer to like parts.

DESCRIPTION OF THE DRAWINGS

FIG. 1 is a top plan view of the novel spinal prosthesis.

FIG. 2 is an end view of the prosthesis shown in FIG. 1.

FIG. 3 is a sectional view taken substantially in the plane of line 3—3 in FIG. 1.

FIG. 4 is an exploded view of the novel prosthesis.

FIG. 5 is a top plan view of the interior of one of the shelves comprising the novel prosthesis.

FIG. 6 is a side elevational view of the shell half shown in FIG. 5.

FIG. 7 is an end view of the shell half shown in FIGS. 5 and 6.

FIG. 8 is a fragmentary view of the shell half shown in FIG. 7, but showing in further detail the half edge shape which is adapted to engage the implant sheath and a circlage wire.

FIG. 9 is an exploded view showing the interiors of the shell halves.

While the invention will be described in connection with a preferred embodiment, it will be understood that it is not intended to limit the invention to this embodiment. On the contrary, it is intended to cover all alternatives, modifications and equivalents as may be included within the spirit and scope of the invention as defined by the appended claims.

To accomplish the objectives set out above, the novel exemplary disc prosthesis 10 includes, as shown in the drawings, a peanut shaped housing 20. The housing 20 includes an upper half housing 22 and a lower half housing 24.

As particularly shown in FIGS. 2, 3, and 4, a plurality of resilient, viscoelastic discs 41, 42 are interposed between the upper half housing 22 and the lower half housing 24 to maintain the housing halves separate from one another and to provide for a defined range of motion between the housing halves and, consequently, for the implant patient's spine. Alternatively, the discs 41, 42 may be made of a suitable hydrogel. The discs can have a relatively soft and resilient interior and a relatively hard and durable exterior. If desired, generally conical bosses or posts 29 can fit into recesses 33 formed in the discs 41, 42 to provide stability and limitation against excessive motion. Also, if desired, these posts 29 can be provided with small passageways 31 to permit the introduction of fluids or gel into the interior of the assembled implant. As shown in FIG. 3, circlage wires 37, 38 or other known devices can be fit into grooves 25 (FIG. 8) formed at the edge of the shell halves 22, 24 so as to attach and retain a fluid retaining sheath 39, as suggested in U.S. Pat. No. 5,674,296.

Ports 31 can be formed in the shell halves 22, 24 to permit lubricating fluids or gels to be introduced into the interior of the assembled implant. The ports 31 can later be sealed by a plug, a screw or the like if desired to prohibit the later expulsion or loss of the introduced fluid or gels. Recesses 47, 48 permit bone ingrowth and consequently firm, permanent attachment of the implant to the mating vertebral bone surfaces.

The prosthetic device 10 can be implanted in the thoracic or lumbar region of the spine through a small surgical opening. One device 20 containing two or more discs 41, 42 may be used, or by placing two such devices 20 in parallel, each containing two or more ovoid discs in series, a full range of motion of the functional spinal unit (FSU) can be achieved. If the discoid material possesses resilient, viscoelastic properties, with the housing being split with the internally placed ovoid discs maintaining the separation of the upper and lower housing members, a cushioning effect may also be realized.

As suggested in FIGS. 5 and 9, each ovoid disc 41, 42 may be partly surrounded and retained by a concave surface 51, 52 formed or contained within the housing, and contoured to accept the upper and lower surface shape of each of the ovoid discs 41, 42 so that the housing 20 comprising the two or more halves or paired shells 23, 24 may slide and/or rotate over the surface of the discs 41, 42 to provide for joint space separation and motion.

The device may be inserted via open or minimally invasive techniques including endoscopy, or by a variety of known surgical anterior, posterior, lateral or other approaches where adequate anatomical space is available. Though the prosthesis is inserted as a single cylindrical unit, its final position is such that one half of the housing is left exclusively in contact with the cephalad vertebral bone with the caudal vertebral bone superior end plate. The discoid vertebral bodies between the cylindrical housing halves contain two or more concave surfaces, allow movement by providing for sliding and rotating in multiple directions and cushioning in response to physiological loads placed upon them.

The following is claimed as invention:

1. A disc prosthesis comprising an oblong shell having first and second housing portions and first and second flexible members interposed between the first and second housing portions, respectively, the first and second flexible members including a relatively soft interior and a relatively hard exterior and having viscoelastic properties for sliding engagement with concave surfaces formed in their respective housing portions, and the first and second housing portions including a protrusion for extending into an interior portion of its corresponding flexible member.

2. A disc prosthesis according to claim 1 wherein the first and second flexible members are positioned in a spaced relation to each other and are positioned an equal and opposite distance from a central point of the disc prosthesis.

3. A disc prosthesis comprising an oblong shell having first and second housing portions and first and second flexible members interposed between the first and second housing portions, respectively, the first and second flexible members including a relatively soft interior and a relatively hard exterior, wherein each of said first and second flexible members are of a discoid shape and the shell is of a peanut shape, wherein each of the first and second housing includes a protrusion for extending into an interior of its corresponding discoid shaped flexible member.

* * * * *